United States Patent
Jing et al.

(10) Patent No.: US 7,879,619 B2
(45) Date of Patent: Feb. 1, 2011

(54) APPARATUS FOR DETECTING ONE OR MORE SUBSTANCES AND METHOD OF DETECTING A SUBSTANCE

(76) Inventors: Tianwei Jing, 709 E. Verde La., Tempe, AZ (US) 85284; Feimeng Zhou, 10037 Lynrose St., Temple City, CA (US) 91780; Nongjian Tao, 13571 E. Estrella Ave., Scottsdale, AZ (US) 85259

( * ) Notice: Subject to any disclaimer, the term of this patent is extended or adjusted under 35 U.S.C. 154(b) by 1153 days.

(21) Appl. No.: 11/544,796

(22) Filed: Oct. 6, 2006

(65) Prior Publication Data

US 2007/0082408 A1   Apr. 12, 2007

Related U.S. Application Data

(60) Provisional application No. 60/724,431, filed on Oct. 7, 2005.

(51) Int. Cl.
*G01N 21/41* (2006.01)
*G01N 21/01* (2006.01)

(52) U.S. Cl. ........................ 436/171; 250/573; 250/574; 250/575; 250/576; 356/132; 356/451; 422/82.05; 422/82.09; 422/82.11; 436/46; 436/52; 436/86; 436/94; 436/165

(58) Field of Classification Search ......... 250/573–576; 356/128, 246, 445, 451, 453, 132; 422/82.01, 422/82.05, 82.09, 82.11; 436/46, 52, 73, 436/86, 94, 165, 171
See application file for complete search history.

(56) References Cited

U.S. PATENT DOCUMENTS

| | | | |
|---|---|---|---|
| 4,997,278 A | 3/1991 | Finlan et al. | |
| 5,035,863 A * | 7/1991 | Finlan et al. | 422/82.05 |
| 5,064,619 A | 11/1991 | Finlan | |
| 5,341,215 A * | 8/1994 | Seher | 356/445 |
| 5,485,277 A * | 1/1996 | Foster | 356/445 |
| 5,508,809 A * | 4/1996 | Peacock et al. | 356/445 |
| 5,822,073 A * | 10/1998 | Yee et al. | 356/445 |
| 5,858,799 A | 1/1999 | Yee et al. | |
| 5,875,032 A | 2/1999 | Naya | |

(Continued)

OTHER PUBLICATIONS

Berger, C. H. E. et al, Analytical Chemistry 1998, 70, 703-706.*

(Continued)

*Primary Examiner*—Arlen Soderquist
(74) *Attorney, Agent, or Firm*—Bryan Cave LLP (57) ABSTRACT

An apparatus for detecting one or more substances includes a radiation source emitting a beam of radiation and also includes a material capable of reflecting the beam of radiation with a first characteristic and capable of reflecting the beam of radiation with a second characteristic when the material interacts with the one or more substances. The apparatus also includes two or more radiation detectors to detect the first and second characteristics of the beam of radiation. A first one of the two or more radiation detectors is adjustably aligned to detect the first and second characteristics of the beam of radiation reflected from a first region of the material. A second one of the two or more radiation detectors is adjustably aligned to detect the first and second characteristics of the beam of radiation reflected from a second region of the material.

44 Claims, 5 Drawing Sheets

U.S. PATENT DOCUMENTS

| | | | | |
|---|---|---|---|---|
| 5,955,729 | A | * | 9/1999 | Nelson et al. ............... 250/282 |
| 6,111,248 | A | * | 8/2000 | Melendez et al. ........... 250/239 |
| 6,188,813 | B1 | * | 2/2001 | Dourdeville et al. .......... 385/12 |
| 6,342,948 | B1 | * | 1/2002 | Gilby ......................... 356/436 |
| 6,570,657 | B1 | * | 5/2003 | Hoppe et al. ................ 356/445 |
| 6,628,376 | B1 | * | 9/2003 | Nikitin et al. .................. 356/38 |
| 6,649,361 | B1 | | 11/2003 | Iwasaki et al. |
| 6,738,141 | B1 | * | 5/2004 | Thirstrup .................... 356/445 |
| 6,741,352 | B2 | | 5/2004 | Naya |
| 6,784,999 | B1 | | 8/2004 | Tao et al. |
| 6,803,205 | B2 | * | 10/2004 | Duffy et al. .................... 435/15 |
| 6,849,397 | B2 | * | 2/2005 | Nelson et al. .................. 435/5 |
| 6,862,094 | B2 | * | 3/2005 | Johansen .................... 356/445 |
| 6,862,398 | B2 | * | 3/2005 | Elkind et al. ................ 356/445 |
| 6,867,857 | B2 | * | 3/2005 | Hobbs ........................ 356/246 |
| 6,956,651 | B2 | * | 10/2005 | Lackritz et al. ............. 356/445 |
| 6,982,819 | B2 | * | 1/2006 | Sawin et al. ................ 359/245 |
| 7,027,159 | B2 | * | 4/2006 | Naya .......................... 356/445 |
| 7,046,357 | B2 | * | 5/2006 | Weinberger et al. ......... 356/246 |
| 7,084,980 | B2 | * | 8/2006 | Jones et al. ................. 356/445 |
| 7,148,968 | B2 | * | 12/2006 | Codner et al. ............... 356/445 |
| 7,187,444 | B2 | * | 3/2007 | Naya et al. .................. 356/445 |
| 7,187,446 | B2 | * | 3/2007 | Kimura ....................... 356/445 |
| 7,193,703 | B2 | * | 3/2007 | Hakamata et al. ........... 356/246 |
| 2007/0082408 | A1 | | 4/2007 | Jing et al. |

OTHER PUBLICATIONS

Boussaad, S. et al, Analytical Chemistry 2000, 72, 222-226.*
Wang, S. et al, Analytical Chemistry 2000, 72, 4003-4008.*
Naimushin, A. N. et al, Biosensors and Bioelectronics 2002, 17, 573-584.*
Song, F. et al, Nucleic Acids Research 2002, 30, e72.*
Kang, X. et al, Langmuir 2002, 18, 10305-10310.*
Zhang, H. Q. et al, Review of Scientific Instruments 2003, 74, 150-153.*
Li, L. et al, Langmuir 2003, 19, 2974-2982.*
Shumaker-Parry, J. S. et al, Analytical Chemistry 2004, 76, 907-917.*
Yao, X. et al, Journal of Physical Chemistry B 2004, 108, 7206-7212.*
Ikehata, A. et al, Analytical Chemistry 2004, 76, 6461-6469.*
Campagnolo, C. et al, Journal of Biochemical and Biophysical Methods 2004, 61, 283-298.*
Forzani, E. S. et al, Environmental Science Technology 2005, 39, 1257-1262.*
Zybin, A. et al, Analytical Chemistry 2005, 77, 2393-2399.*
Liedberga, B. et al, Sensors and Actuators 1983, 4, 299-304.*
Matsubara, K. et al, Applied optics 1988, 27, 1160-1163.*
Renn, C. N. et al, Analytical Chemistry 1988, 60, 1188-1193.*
Kooyman, R. P. H. et al, Analytical Chemistry 1991, 63, 83-85.*
Sjolander, S. et al, Analytical Chemistry 1991, 63, 2338-2345.*
Garabedain, R. et al, Sensors and Actuators A 1994, 43, 202-207.*
Pierce, M. et al, Langmuir 1994, 10, 3217-3221.*
Chou, C. et al, International Journal of Machine Tools & Manufacture 1997, 37, 579-590.*
O'Brien II, M. J. Biosensors & Bioelectronics 1999, 14, 145-154.*
Golnabi, H., Optics & Laser Technology 2000, 32, 311-316.*
Shon, Y.-S. et al, Journal of the American Chemical Society 2000, 122, 7556-7563.*
Nikitin, P. I. et al, Sensors and Actuators A 2000, 85, 189-193.*
Ji. H.-F. et al, Analytical Chemistry 2001, 73, 1572-1576.*
Pietrement, O. et al, Langmuir 2001, 17, 6540-6546.*
Furuki, M. et al, Sensors and Actuators B 2001, 79, 63-69.*
Gao, W. et al, Precision Engineering 2002, 26, 396-404.*
Palumbo, M. et al, Sensors and Actuators B 2003, 90, 264-270.*
Zhang, Y. et al, Analytical Chemistry 2003, 75, 4773-4777.*
Makynen, A. et al, Sensors and Actuators A 2003 105, 261-270.*
Hosoda, H. et al, Journal of Physical Chemistry A 2004, 108, 1461-1464.*
Tang, Y. et al, Analytical Chemistry 2004, 76, 2478-2481.*
Wang, Q. et al, Biomacromolecules 2004, 5, 1356-1361.*
Kooyman, R. P. H., Encyclopedia of Spectroscopy and Spectrometry, 2004, 2302-2310.*
Tian, F. et al, Analytical Chemistry 2005, 77, 1601-1606.*
Kurita et al., "Electrochemical Surface Plasmon Resonance Measurement in a Microliter Volume Flow Cell for Evaluating the Affinity and Catalytic Activity of Biomolecules", Anal. Chem. 79 (24), pp. 9572-9576; Dec. 15, 2007.
Blikstad et al., "Detection and Characterization of Oligosaccharides in Column Effluents Using Surface Plasmon Resonance", Analytical Biochemistry 233, pp. 42-49, Jun. 15, 1995.
Du et al., "Postcolumn Renewal of Sensor Surfaces for High-Performance Liquid Chromatography#Surface Plasmon Resonance Detection", Anal. Chem. 80 (11), pp. 4225-4230, Jun. 1, 2008.
Whelan et al., "Surface Plasmon Resonance Detection for Capillary Electrophoresis Separations", Anal Chem. 75 (6), pp. 1542-1547, Mar. 15, 2003.
Abeles et al., "Investigation of the Metal—Electrolyte Interface Using Surface Plasma Waves with Ellipsometric Detection", Solid State Communication, vol. 16, pp. 843-847, 1975.
Brod et al., "Electrical Control Over Antibody—Antigen Binding", ScienceDirect, Sensors and Actuators B 128, pp. 560-565, 2007.
Cepria et al., "Surface Plasmon Resonance-Based Detection, An Alternative to Refractive Index Detection in High-Performance Liquid Chromatography", Journal of Chromatography A 759, pp. 27-35, 1996.
Heaton et al., "Electrostatic Surface Plasmon Resonance: Direct Electric Field-Induced Hybridization and Denaturation in Monolayer Nucleic Acid Films and Label-Free Discrimination of Base Mismatches", PNAS, vol. 98, No. 7, pp. 3701-3704, Mar. 27, 2001.
Ly et al., "Integrated Label-Free Protein Detection and Separation in Real Time Using Confined Surface Plasmon Resonance Imaging", Anal. Chem., 79 (6), pp. 2546-2551, Mar. 15, 2007.
Nice et al., "Synergies Between Micropreparative High-Performance Liquid Chromatography and an Instrumental Optical Biosensor", Journal of Chromatography A, 660, pp. 169-185, 1994.
Wang et al., "Detection of Heavy Metal Ions in Water by High-Resolution Surface Plasmon Resonance Spectroscopy Combined with Anodic Stripping Voltammetry", Anal. Chem., 79 (12) pp. 4427-4432, Jun. 15, 2007.
Kretschmann, "The ATR Method With Focused Light-Application to Guided Waves on a Grating", Optics Communications, vol. 26, Issue 1, pp. 41-44, 1978.
Richards et al., "Surface-Plasmon Excitation Using a Polarization-Preserving Optical Fiber and an Index-Matching Fluid Optical-Cell", Applied Optics, vol. 32, Issue 16, pp. 2901-2906, Jun. 1, 1993.
Tao et al., "High Resolution Surface Plasmon Resonance Spectroscopy", Review of Scientific Instruments, vol. 70, Issue 12, pp. 4656-4660, Dec. 1999.

* cited by examiner

APPARATUS FOR DETECTING ONE OR MORE SUBSTANCES AND METHOD OF DETECTING A SUBSTANCE

CROSS-REFERENCE TO RELATED APPLICATION

This application claims the benefit of U.S. Provisional Application Ser. No. 60/724,431, filed Oct. 7, 2005.

FIELD OF THE INVENTION

This invention relates generally to the detection of a substance, and relates more particularly to an apparatus and a method for detecting a substance by detecting changes in the characteristic of a reflected beam of radiation.

BACKGROUND OF THE INVENTION

For decades, researchers have been developing techniques to more accurately and more quickly detect the presence and concentration of a chemical, a gas, a liquid, or other substance. For example, surface plasmon resonance (SPR) is one well-known technique that researches have been using for such detection in a wide variety of areas including, but not limited to, life science research, drug discoveries, electroanalysis and electrochemical applications, environmental science, chemical sensor development, biosensor development, surface characterizations, and food quality, safety, and other analysis. More specifically, in biomedical diagnostics, researchers use SPR to detect antibodies associated with bacteria or a virus to determine the existence of an infection, and researchers also use SPR for gene probes to detect the presence of specific deoxyribonucleic acid (DNA) sequences or ribonucleic acid (RNA) sequences in analytes or other buffer solutions. As another more detailed example, researchers use SPR to detect trace amounts of toxic agents in the air and in water for environmental protection applications or for chemical or biological warfare applications.

Despite the widespread applications for SPR, current SPR techniques still suffer from two major drawbacks: slow response time and limited angular resolution. The first problem prevents the current SPR techniques from detecting fast SPR processes, such as those processes occurring during (a) the initial adsorption of molecules onto surfaces, (b) fast interactions or reactions between surface bound molecules and molecules in solution, and (c) fast conformational changes in adsorbed proteins. The second problem limits the sensitivity of current SPR techniques from detecting small quantities of molecules or small structural or conformational changes in molecules.

In micro-fluidic SPR applications, additional problems typically occur. For example, the background signal often drifts due to temperature and other undesirable fluctuations, which limit the accuracy of the SPR measurement. Additionally, air bubbles and other impurities in the buffer solution also cause many unpredictable changes in the SPR measurement, which prevents the detection of small changes.

Accordingly, a need still exists a detection apparatus and method of detection that overcomes these significant drawbacks.

BRIEF DESCRIPTION OF THE DRAWINGS

The invention will be better understood from a reading of the following detailed description, taken in conjunction with the accompanying figures in the drawings in which.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments of the invention described herein are, for example, capable of operation in sequences other than those illustrated or otherwise described herein. Furthermore, the terms "comprise," "include," "have," and any variations thereof, are intended to cover a non-exclusive inclusion, such that a process, method, article, or apparatus that comprises a list of elements is not necessarily limited to those elements, but may include other elements not expressly listed or inherent to such process, method, article, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein. The term "coupled," as used herein, is defined as directly or indirectly connected in an electrical, mechanical, or other manner.

DETAILED DESCRIPTION OF THE DRAWINGS

In a first embodiment, an apparatus for detecting one or more substances includes a radiation source emitting a beam of radiation and also includes a material capable of reflecting the beam of radiation with a first characteristic and capable of reflecting the beam of radiation with a second characteristic when the material interacts with the one or more substances. The apparatus also includes two or more radiation detectors to detect the first and second characteristics of the beam of radiation. A first one of the two or more radiation detectors is adjustably aligned to detect the first and second characteristics of the beam of radiation reflected from a first region of the material. A second one of the two or more radiation detectors is adjustably aligned to detect the first and second characteristics of the beam of radiation reflected from a second region of the material.

In a second embodiment, the apparatus uses surface plasmon resonance (SPR) to detect the presence and absence of molecules on or near a surface of a metallic layer, as well as structural and electronic changes in the molecules. SPR is created by exciting collective oscillations of free electrons in a metallic layer. More specifically, the apparatus also includes a light projection system including a light beam source and an optional optical assembly to project a light beam towards the metallic layer. The apparatus further includes a light detection system including at least two light beam sensors, or position sensitive photodetectors (PSDs), and an optional optical assembly. As an example, the light beam sensors can be the only adjustable component in the apparatus. The apparatus can also include a dielectric body to support the metallic layer, where the light beam is transmitted through a first portion of the dielectric body, reflected off of the metallic layer, and transmitted through a second portion of the dielectric body and towards the light detection system.

In the first and second embodiments, the apparatus can also include an assembly having a holder, a cell, and a gasket, which are mounted collectively onto the metallic layer, dielectric body, and/or other structure supporting the metallic layer and/or dielectric body. Alternatively, the holder, cell, and gasket can form a separate apparatus. In one embodiment, the cell and gasket each have two or more flow channels, and in another embodiment, the cell and gasket each have one flow channel while the metallic layer is divided into two or more separate regions. The flow channel(s) are aligned to the regions of the metallic layer off of which the radiation or light beam is internally reflected. The radiation or light beam detectors detect the reflection of the radiation or light beam, and, as an example, the light beam detection system determines the change(s) in the SPR angle of the reflected light beam and the molecular binding or other events causing such change(s).

The apparatuses described herein can be used in biomedical applications, chemical applications, life science research, DNA sequencing, ligand-receptor recognition, drug discoveries, electroanalysis, electrochemical applications, impedance analysis, fluorescence detection, molecular binding detection, environmental science, chemical sensors, biosensors, surface characterizations, and food quality, safety, and other analysis. As explained herein, the apparatuses have high resolution, stability, and a fast response time, and the apparatuses are also easy to use and flexible.

Figure 1:
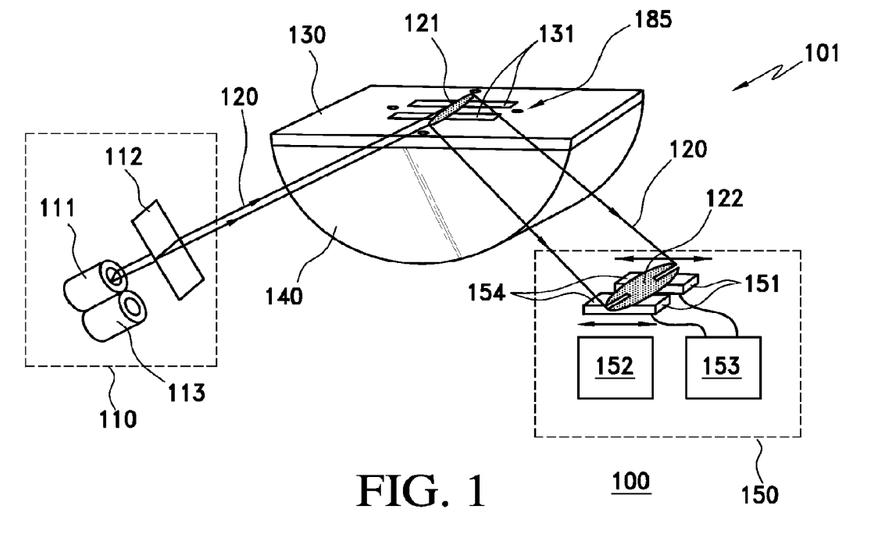
FIG. 1 illustrates a schematic view of a first portion of an apparatus in accordance with an embodiment of the invention.

FIG. 1 illustrates a schematic view of a first portion 101 of an apparatus 100. Apparatus 100 is used to detect one or more substances. As a general overview, apparatus 100 includes a light projection system to condition a light beam or other radiation into a line and projects the line onto a metallic layer or other material. Apparatus 100 can also include multiple position sensitive detectors (PSDs) to detect the internal reflection of the incident light or other radiation from the multiple regions of the material. Preferably, the detectors detect the total internal reflection of the incident light or radiation. Portion 101 can be referred to as the detection portion of apparatus 100.

Apparatus 100 can be a modification of the Kretschmann configuration used to create and measure SPR. In this configuration, plasmons in the metallic layer resonate with light incident upon the metallic layer at an angle, and the plasmons absorb the light at that angle, which is also referred to as the resonance angle. The binding of molecules to or near the metallic layer, or a change in the molecules bound to the metallic layer, causes a shift in the resonance angle. The amount of the shift is proportional to the number and size of the molecules. By monitoring the shift in the resonance angle over time, apparatus 100 monitors the molecular binding or changing events to permit the study of the same. As explained herein, apparatus 100 achieves both high angular resolution and a fast sampling speed.

Portion 101 of apparatus 100 includes a light or radiation projection system 110 to project a light beam or other beam of radiation 120. System 110 includes a light source or other radiation source 111 to emit radiation 120. In one embodiment, system 110 polarizes radiation 120. Radiation 120 can also be referred to as the incident light or incident radiation.

System 110 can comprise an optional lens assembly 112 comprising one or more lenses to focus radiation 120 at a specific angle onto a metallic layer or other material (described hereinafter), which causes SPR at the interface of the material and the one or more substances. As an example, lens assembly 112 can comprise a single cylindrical lens. In the embodiment illustrated in FIG. 1, system 110 projects radiation 120 as a single beam of radiation on the material.

In the present embodiment, system 110 can include a second light source or other radiation source, such as source 113, to project a second light beam or other beam of radiation onto the material at a different angle than radiation 120. System 110 can also polarize the second beam of radiation. As an example, the second radiation source can be a laser diode. When the one or more substances to be detected by apparatus 100 are in a gas or liquid phase, system 110 can include radiation source 113 to complement source 111 and excite the SPR at the interface of the metallic layer or other material (described hereinafter) and the one or more substances. There can be embodiments where system 110 comprises only a single light or radiation source, such as only one of sources 111 or 113.

Portion 101 of apparatus 100 also includes a material 130 capable of reflecting radiation 120 with a first characteristic and capable of reflecting radiation 120 with a second (and different) characteristic when material 130 interacts with the one or more substances to be detected by apparatus 100. As an example, material 130 can be a metallic layer, and the first and second characteristics can be different SPR angles. As another example, the metallic layer can be a thin film containing metal and other substances, or just metal. As a further example, the metallic layer can be coated with an organic or inorganic substance.

As illustrated in FIG. 1, material 130 is single, continuous, and homogenous piece. As an example, material 130 comprises gold, silver, and/or platinum. However, an assembly (described in later figures) mounted on material 130 can have two channels 131 to expose different regions of material 130 to the one or more substances to be detected by apparatus 100. Accordingly, in the embodiment illustrated in FIG. 1, material 130 has two regions to interact with the one or more substances, but one skilled in the art will understand that material 130 can also have more than two such regions. When material 130 has two or more regions to interact with the same substance, one of the regions can be used to replicate a measurement of a different region, where the different region can have a different coating. Furthermore, one of the regions of material 130 can be used as a reference region or a control that is not exposed to any of the one or more substances to be detected by apparatus 100. The use of one or more reference and/or control regions, and the replicated measurements, can improve the sensitivity and stability of the measurements from apparatus 100.

As illustrated in FIG. 1, system 110 projects radiation 120 as a single beam on the two or more regions of material 130 such that a single light spot 121 shines across all of the two or more regions of material 130. As an example, light spot 121 can have the shape of a line or an ellipse.

In a different embodiment (not illustrated in FIG. 1), material 130 can also have two or more regions to interact with the one or more substances when material 130 is divided into two or more physically separate regions. In this embodiment, each of the regions of material 130 can have the same composition or different compositions, or two or more of the regions of material 130 can have the same composition while one or more of the other regions have different compositions. Also in this embodiment, the regions of material 130 can be electrically isolated from each other and can be electrically and/or electrochemically biased to control, for example, the surface potential of material 130. In one embodiment, the regions of material 130 can even be electrically and/or electrochemically biased independently from each other. When material 130 is divided into two or more physically separate regions, the regions of material 130 can be used to detect the same one of the one or more substances to be detected by apparatus 100; one or more of the regions of material 130 can be used to detect different ones of the one or more substances; and/or one or more of the regions of material 130 can be used as a reference or control region.

Portion 101 of apparatus 100 further comprises a dielectric body 140 located adjacent to material 130. Radiation 120 is transmitted through body 140 to material 130. Body 140 can be a prism to further focus radiation 120 towards the two or more regions of material 130. As an example, the prism can be a hemicylindrical prism. More specifically, the prism can be a right-angle or equilateral hemi-cylindrical prism having a smooth, curved surface facing towards system 110 and a smooth, planar surface facing towards material 130. Preferably, body 140 has a high index of refraction that is greater than the index of refraction of air. For example, body 140 can be comprised of a dielectric such as boron potassium (e.g., $BK_7$) or sulfur fluoride (e.g., $SF_{10}$). As an other example, body 140 can be comprised of a composite structure of an index matching medium located between two dielectric layers. In this example, the index matching medium can be a fluid, an oil, a gel, or a gas.

In one embodiment, body 140 supports material 130. For example, material 130 can be coated on the top surface of body 140 using an evaporation technique, chemical vapor deposition technique, or the like. In another embodiment, material 130 can be coated over a glass plate or other transparent or radiation-conductive plate, and the plate can be supported by the top surface of body 140. In yet another embodiment, the plate can be a portion of the composite structure for body 140.

Portion 101 of apparatus 100 also comprises a light or radiation detection system 150. System 150 includes two or more light beam sensors or other radiation detectors 151. Detectors 151 are preferably identical to each other. When radiation 120 is a light beam, detectors 151 are preferably photodetectors. Detectors 151 are preferably not charge coupled devices (CCDs) or linear diode arrays (LDAs), which operate slowly compared to photodetectors. In a different embodiment, system 150 includes a single radiation detector.

Detectors 151 can be located adjacent to each other and can detect the first and second characteristics of radiation 120 after being reflected from the two or more regions of material 130 and transmitted through body 140. More specifically, a first one of detectors 151 detects the first and second characteristics of radiation 120 reflected from a first region of material 130, and a second one of detectors 151 detects the first and second characteristics of radiation 120 reflected from a second region of material 130. Furthermore, the first one of detectors 151 does not detect the portion of radiation 120 reflected from the second region of material 130, and the second one of detectors 151 does not detect the portion of radiation 120 reflected from the first region of material 130. In one embodiment, each of detectors 151 can generate an SPR signal based on the portion of radiation 120 detected by the detector. After radiation 120 is reflected from material 130, radiation 120 can also be referred to as the reflected light or reflected radiation. In an embodiment where system 110 includes a second radiation source, detectors 151 can also detect the second beam of radiation in the same manner that detectors 151 detect radiation 120.

In one embodiment, detectors 151 have substantially planar surfaces 154, and the surface of material 130 off of which radiation 120 is reflected is also substantially planar. Furthermore, each of surfaces 154 can be positioned to be substantially perpendicular to the direction of radiation 120 as radiation 120 is being detected by detectors 151. In one embodiment, surfaces 154 of detectors 151 are also substantially perpendicular to the direction of gravity to provide more accurate and reliable placement of detectors 151.

System 150 also includes actuators 152 to adjustably align detectors 151 relative to material 130 and body 140 to detect radiation 120. In this embodiment, detectors 151 can be position sensitive detectors (PSDs). As an example, a PSD can comprise a monolithic p-type, intrinsic, n-type (PIN) photodiode having a uniform resistance in one or two dimensions. PSDs are different from standard photodetectors because PSDs provide continuous detection of a change in the position of radiation 120, while standard photodetectors do not provide such continuous detection. PSDs also have other advantages, compared to discrete element detectors, including high position resolution, fast response speed, and simple operating circuits. In addition, the position data from a PSD is independent of the size of the light spot shining on the PSD.

The position of each of detectors 151 can be aligned independently of each other such that light spot 122 shines in the middle of each of detectors 151. In this manner, detectors 151 can detect a larger variation in the SPR angle of radiation 120. Actuators 152 can include mechanical motors, electrical motors, piezoelectric motors, or the like. Actuators 152 can also be operated by hand. In one embodiment, detectors 151 are the only movable components of apparatus 100 to improve the stability of apparatus 100.

Light spot 122 has two or more dark spots that correspond to the SPR occurring at the two or more regions of material 130 reflecting radiation 120 toward detectors 151. Preferably, detectors 151 are aligned such that the dark spots are located within the middle of each of detectors 151 at the beginning of the measurement. The movement of the dark spots during the measurement signifies molecular binding at the interface of material 130 and the one or more substances to be detected by apparatus 100, and the movement can also signify other electronic or structural changes in the molecules bound to the interface. In the embodiment where detectors 151 are photodetectors, detectors 151 can measure the location of the dark spots or the dip in intensity of the light beam more quickly and accurately. Also, in the embodiment where detectors 151 are position sensitive photodetectors, detectors 151 can be used to measure only the horizontal (i.e., "X") movement or only the vertical (i.e., "Y") movement of the dark spot across detectors 151, and not both the horizontal and the vertical movement and not the absolute location of the dark spot. By measuring only the position shift of the dark spot, apparatus 100 provides a highly sensitive and quick detection scheme that can measure extremely small changes in the SPR angle.

System 150 also includes a computation module 153 to receive SPR signals from detectors 151, to interpret and/or calibrate the SPR signals, and to indicate a change in the SPR at an interface between material 130 and the one or more substances to be detected by apparatus 100. As an example, module 153 can indicate the change in the SPR based on a change in the SPR signals. More specifically, the change in the SPR can occur when the SPR signal changes from its first characteristic to its second characteristic. The change in the SPR can signify a change in the molecular binding at the interface of material 130 and/or other electronic or structural changes at the interface.

In a different embodiment, module 153 can be separate from system 150. In the same or another embodiment, module 153 can also generate and/or condition the SPR signal, while detectors 151 generate a more basic output signal that is transmitted to module 153. In an embodiment where one region of material 130 is used as a reference region and/or as a control region, the corresponding SPR signal is used as a reference signal and/or a control signal to compensate for thermal, optical, electronic, mechanical, acoustic noise, drift, and other background considerations. In this embodiment, the measurement sensitivity of apparatus 100 has been demonstrated to be improved by a factor of ten compared to prior art systems.

Figure 2:
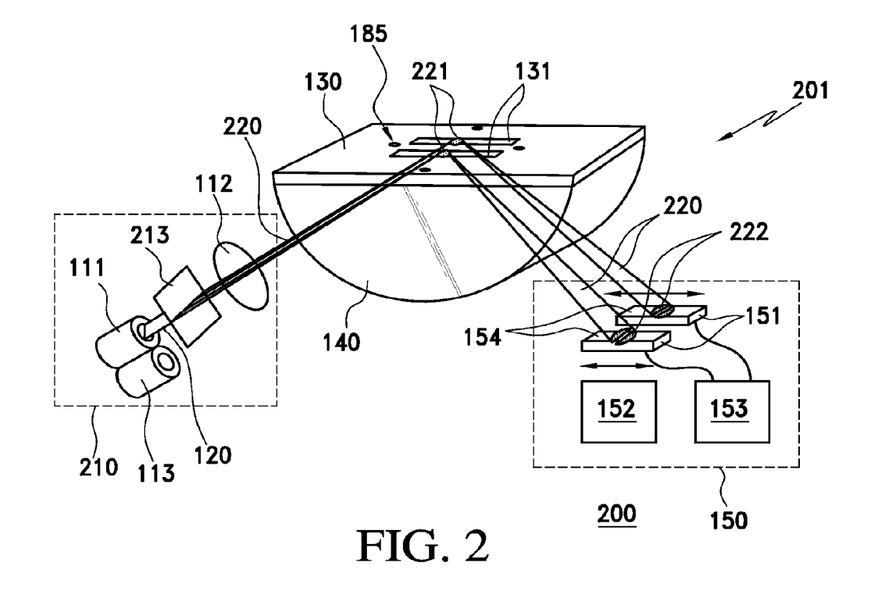
FIG. 2 illustrates a schematic view of the first portion of the apparatus in accordance with a different embodiment of the invention.

Turning to the next figure, FIG. 2 illustrates a schematic view of a first portion 201 of an apparatus 200, which is a similar, but different, embodiment of apparatus 100 in FIG. 1. In particular, portion 201 of apparatus 200 includes material 130, body 140, and system 150, as in portion 101 of apparatus 100 in FIG. 1. However, portion 201 of apparatus 200 in FIG. 2 includes a light or radiation projection system 210, which is similar to, but different from, system 110 in apparatus 100 in FIG. 1.

More specifically, system 210 in FIG. 2 includes an additional beam splitter 213 located between source 111 and assembly 112 to split radiation 120 into two or more beams or portions of light or radiation 220. As an example, beam splitter 213 can include a lateral displacement prism and a beam defocusing mechanism. Preferably, all portions of radiation 220 pass through the same guides and are reflected from the same reflectors in apparatus 200 to improve the sensitivity, accuracy, consistency, and stability of the measurements from apparatus 200.

In one embodiment, assembly 112 and material 130 can be adjusted such that radiation 220 are slightly defocused to have two or more light spots 221 on the two or more regions of material 130. Light spots 221 are reflected from the regions of material 130 and detected by detectors 153 as light spots 222. The use of a single light or radiation source (i.e., source 111) to generate radiation 220 eliminates intensity fluctuations in different regions of the light source, which improves the sensitivity, accuracy, consistency, and stability of the measurements from apparatus 200.

Furthermore, in a different embodiment, system 210 in FIG. 2 can include a second light source, as indicated previously with respect to system 110 in FIG. 1. In this embodiment, the second light source can project one or more additional light beams onto the same region(s) of material 130 on which light spots 221 are projected, but where the one or more additional light beams are projected onto material 130 at a different angle. In another embodiment of FIG. 2, system 210 can be configured to split radiation 120 into two or more beams or portions of light or radiation where each beam of radiation is projected onto the same region of material 130 at a different angle. In each of these embodiments, a single radiation detector detects each beam of radiation reflected from the same region of material 130. As an example, this embodiment improves the flexibility of apparatus 100 such that it can be used for gas and fluid detection where one beam of radiation at one incident angle is used for gas detection and a different beam of radiation at a different incident angle is used for fluid detection.

Figure 3:
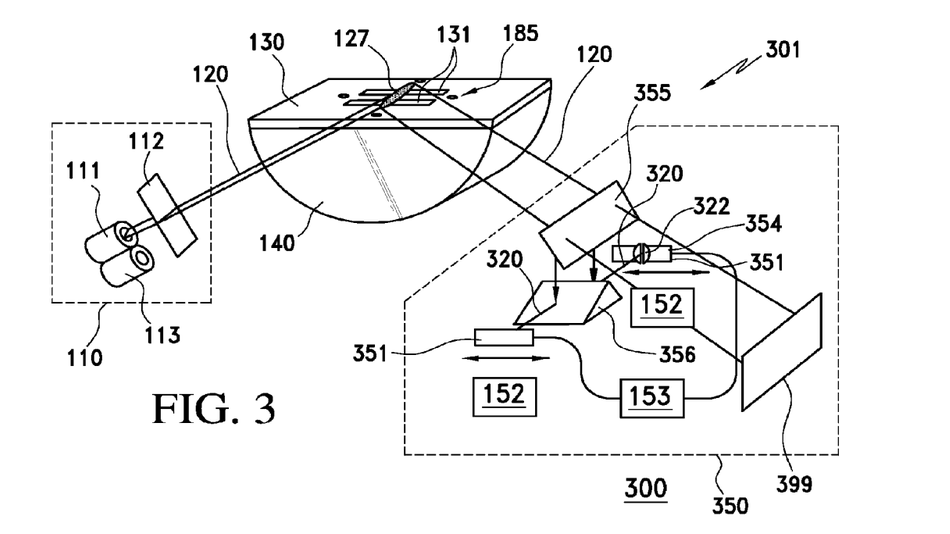
FIG. 3 illustrates a schematic view of the first portion of the apparatus in accordance with another embodiment of the invention.

Turning to the next figure, FIG. 3 illustrates a schematic view of a first portion 301 of an apparatus 300, which is a similar, but different, embodiment of apparatus 100 in FIG. 1. In particular, portion 301 of apparatus 300 includes system 110, material 130, and body 140, as in portion 101 of apparatus 100 in FIG. 1. In one embodiment of portion 301 of apparatus 301, system 110 can be replaced with system 210 in FIG. 2. Additionally, portion 301 of apparatus 300 in FIG. 3 includes a light or radiation detection system 350, which is similar to, but different from, system 150 in apparatus 100 in FIG. 1.

More specifically, system 350 in FIG. 3 includes a reflector 355 to reflect radiation 120 after radiation 120 is reflected from the regions of material 130. System 350 can also includes an optional splitter 356 to split radiation 120 into two or more beams or portions of light or radiation 320. Splitter 356 splits radiation 120 into radiation 320 after radiation 120 is reflected from reflector 355. Splitter 356 can also be referred to as a reflector, and in one embodiment, splitter 356 can be a right-angle reflector to provide symmetrical distribution of radiation 120 into radiation 320.

In a first embodiment, reflector 355 is a fully reflective mirror. In a second embodiment, reflector 355 is a partially transparent mirror. In this second embodiment, system 350 can also include an imaging device 399 such that a portion of radiation 120 is transmitted through, and not reflected from, reflector 355 towards imaging device 399. Imaging device 399 can be a screen on which radiation 120 is displayed to provide a visual inspection of the quality of the SPR at the interface between material 130 and the one or more substances to be measured. Alternatively, imaging device 399 can be a more complex device such as a video monitor or the like.

System 350 further includes detectors 351 having surfaces 354, which are similar to detectors 151 and surfaces 154, respectively, in FIG. 1, except that surfaces 354 are substantially parallel to the direction of gravity and substantially perpendicular to the direction of radiation 320 as radiation 320 is being detected by detectors 351 as spots 322. Detectors 351 are located apart from each other. More specifically, detectors 351 are located at opposite sides of reflector 355 and splitter 356. Actuators 152 and computation module 153 interact with detectors 351 in a manner similar to that described for detectors 151 in FIG. 1. In the embodiment where system 350 does not include splitter 356, detectors 351 can located adjacent to each other.

Figure 4:
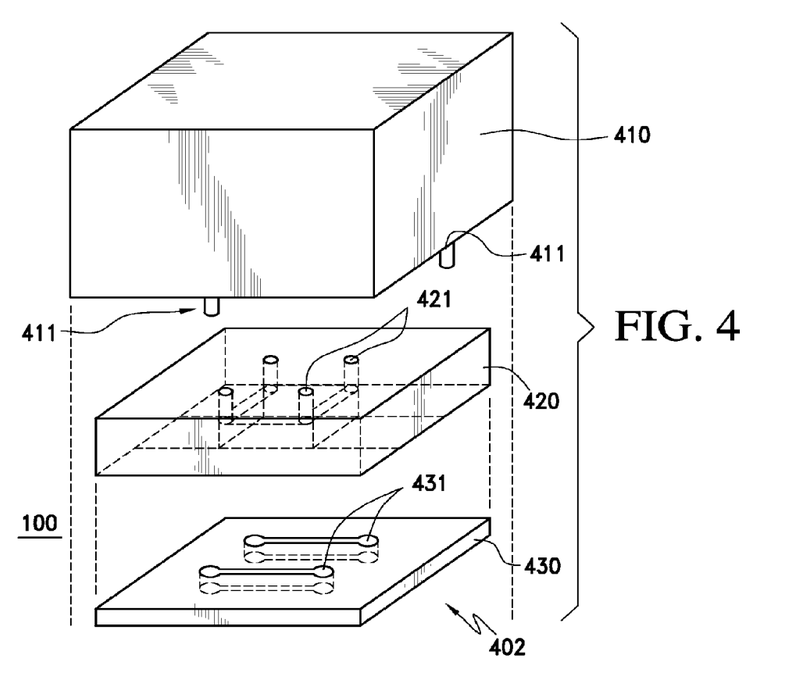
FIG. 4 illustrates an exploded schematic view of a second portion of the apparatus in accordance with an embodiment of the invention.

FIG. 4 illustrates an exploded, schematic view of a second portion 402 of apparatus 100 in FIG. 1. Second portion 402 of apparatus 100 in FIG. 4 is used with first portion 101 of apparatus 100 in FIG. 1, but can also be used with first portion 201 of apparatus 200 in FIG. 2 and first portion 301 of apparatus 300 in FIG. 3. In one embodiment, portion 402 in FIG. 4 is a separate apparatus from first portions 101, 201, and 301 in FIGS. 1, 2, and 3, respectively.

Portion 402 of apparatus 100 comprises an assembly, which includes a frame or other holder 410, a cell 420, and a gasket 430. As an example, the assembly conducts one or more analytes or other buffer solutions containing the one or more substances to be detected by apparatus 100 to the regions of material 130 (FIG. 1) on which light spot 121 (FIG. 1) is shown. Portion 402 can be referred to as a sample portion of apparatus 100.

Holder 410 supports and seals cell 420 and gasket 430 over material 130 and body 140 of portion 101 in apparatus 100 in FIG. 1. As an example, cell 420 and gasket 430 fit within holder 410. In one embodiment, cell 420 and gasket 430 are removable from and replaceable in holder 410, and holder 410 can support and seal other cells and gaskets over material 130 and body 140 of portion 101 in apparatus 100 in FIG. 1.

Cell 320 can include two or more flow channels 421 through which the one or more substances are conducted towards and away from the regions of material 130 to permit the one or more substances to be detected by apparatus 100. The same substance can be conducted through each of channels 421 to provide redundant measurements and improved accuracy; a different substance can be conducted through each of channels 421 to provide faster through-put and cycle-time; the same substance can be conducted through two or more of channels 421 while a different substance can be conducted through one or more of channels 421; and/or one or more of channels 421 can remain empty or can be filled with an inert gas or liquid to serve as a reference and/or control channel. In one embodiment, cell 320 can be comprised of polyetheretherketone (PEEK).

Gasket 430 has one or more openings to expose material 130 to the one or more substances to be detected by apparatus 100. For example, as illustrated in FIG. 4, gasket 430 has two or more channels 431 through which the one or more substances are conducted from cell 420 towards and away from the regions of material 130 (FIG. 1). Channels 431 extend completely through gasket 430 and correspond with, and are coupled to, channels 421 in cell 420 to permit the one or more substances to be conducted through cell 420 and through gasket 430 to interact with the regions of material 130 (FIG. 1). More specifically, channels 421 and 431 in FIG. 4 correspond to channels 131 in FIG. 1. As an example, gasket 430 comprises a soft or deformable material to provide a seal between material 130 (FIG. 1) and cell 420.

The assembly aligns the one or more substances to be detected by apparatus 100 to light spot 121 and/or representative channels 131 in portion 101 of apparatus 100 (FIG. 1). For example, holder 410 can align cell 420 and gasket 430 to material 130. In particular, holder 410 can have a self-alignment mechanism 411, such as the pin structure located at a periphery of holder 410, that corresponds to a complementary self-alignment mechanism 185, such as the hole structure in material 130 and/or body 140, or vice versa. In this embodiment, holder 410 can be a spring-loaded such that pre-alignment of holder 410 and affixing holder 410 with screws are not necessary. As a different example, gasket 430 and/or cell 420 can have the self-alignment mechanism to align channels 431 and 421 to the regions of material 130.

The assembly, including cell 420, can include liquid flow cells, electrochemical cells, gas flow cells, and the like, which are explained in more detail in subsequent figures. The removability of cell 420 and gasket 430 with other cells and gaskets, permits holder 410 to facilitate the installation and high-throughput analyses of different systems of interest. In an embodiment where cell 420 is a gas flow cell to detect small organic molecules in the gas phase, cell 420 can be coupled to material 130 (FIG. 1) and body 140 (FIG. 1) using finger-tight, stainless steel fittings, and an injector valve and a rubber o-ring can be used to allow a gas stream of moderate pressure (i.e., about fifty pounds per square inch) to be delivered to material 130.

Additionally, although not illustrated in FIG. 4, the assembly can also include one or more input ports to introduce the one or more substances into the assembly, one or more output ports to remove the one or more substances from the assembly, one or more ports to degas the buffer solutions containing the one or more substances with an inert gas (i.e., to remove air bubbles from the buffer solutions), one or more ports to keep the one or more substances under an inert gas atmosphere, and/or a pre-conditioning mechanism. As an example, the pre-conditioning mechanism can be used to remove impurities such as dust and/or air bubbles from the one or more substances to be detected by apparatus 100 and/or from the analytes or other buffer solutions containing the one or more substances to improve the sensitivity and stability of apparatus 100. The pre-conditioning mechanism can also be used to degas the buffer solution(s) for at least the same reasons. In one embodiment, the pre-conditioning mechanism can comprise a mechanical vibration mechanism, an acoustic agitation mechanism, a radiation mechanism, and/or a filter mechanism. The pre-conditioning mechanism can be a separate component from the other portions of the assembly.

Figure 5:
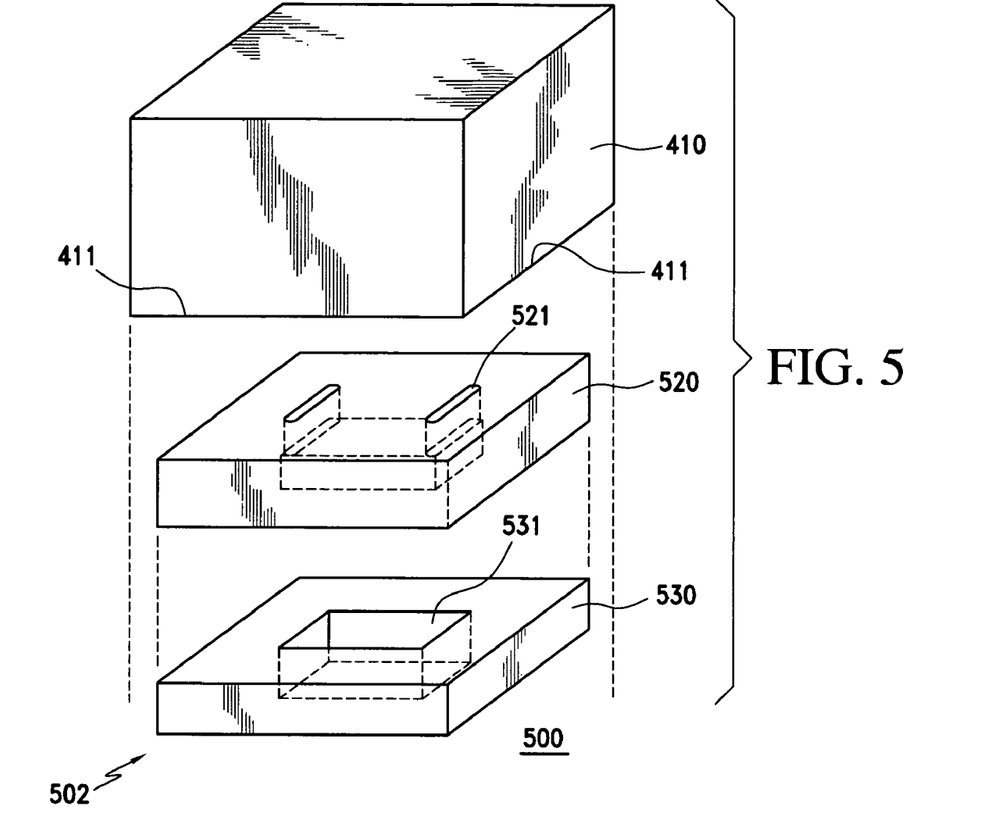
FIG. 5 illustrates an exploded schematic view of the second portion of the apparatus in accordance with a different embodiment of the invention.

FIG. 5 illustrates a schematic view of a second portion 502 of apparatus 500. Second portion 502 in FIG. 5 is a different embodiment of second portion 402 in FIG. 4. A first portion of apparatus 500 can be similar to first portion 101 of apparatus 100, except that material 130 (FIG. 1) is divided into two or more physically separate regions, as explained previously. Accordingly, second portion 502 in FIG. 5 can be used with first portion 101 in FIG. 1, first portion 201 in FIG. 2, and/or first portion 301 in FIG. 3, as modified above. In one embodiment, second portion 502 is a separate apparatus from first portions 101, 201, and 301 in FIGS. 1, 2, and 3, respectively.

As illustrated in FIG. 5, second portion 502 of apparatus 500 includes holder 410. Portion 502 also includes a cell 520, which is similar to cell 420 in FIG. 4, except that cell 520 has a single channel 521. Additionally, portion 502 includes a gasket 530, which is similar to gasket 430 in FIG. 4, except that gasket 530 has a single channel 531.

Figure 6:
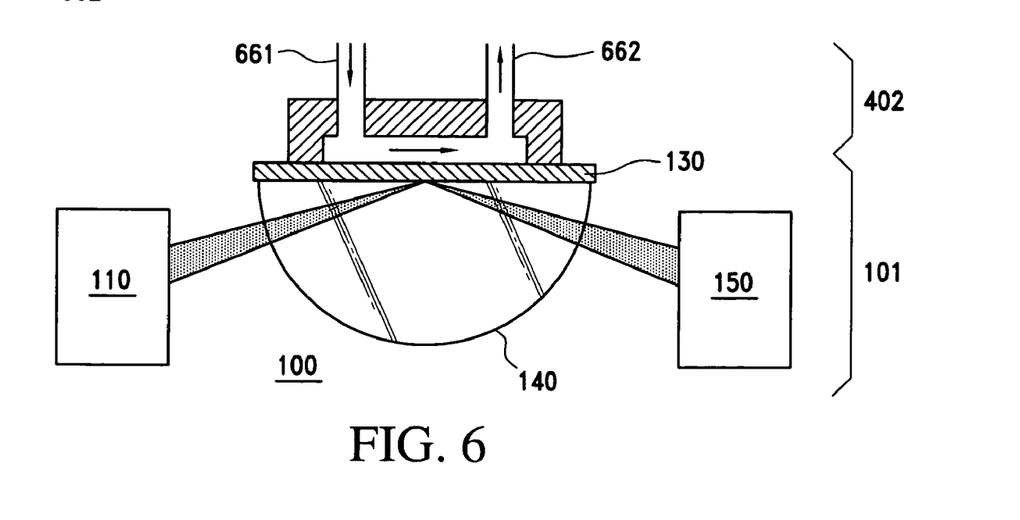
FIG. 6 illustrates a partial cross-sectional, schematic view of the first and second portions of the apparatus in accordance with an embodiment of the invention.

FIG. 6 illustrates a partial cross-sectional, schematic view of first portion 101 (FIG. 1) and second portion 402 (FIG. 4) of apparatus 100, in accordance with a liquid flow cell embodiment. In FIG. 6, portion 402 is illustrated to be a liquid flow cell for liquid phase measurements, and has an input port 661 and an output port 662. As an example, a syringe pump can be coupled to input port 661 to implement a flow injection technique to pump the buffer solution containing the one or more substances to be detected toward material 130. This flow injection technique provides high-throughput analysis, enhanced response times, compact instrumentation, low sample consumptions, and quick start-up and shut-down times. In this embodiment, apparatus 100 can be used in many life science applications including gene assays (e.g., single nucleotide polymorphism, etc.), DNA-DNA interactions, immunosensing (e.g., ligand-receptor, antibody-antigen, etc.), DNA-protein interactions, protein-protein interactions, protein-drug interactions, protein unfolding, protein conformational changes, and drug discovery and development.

Figure 7:
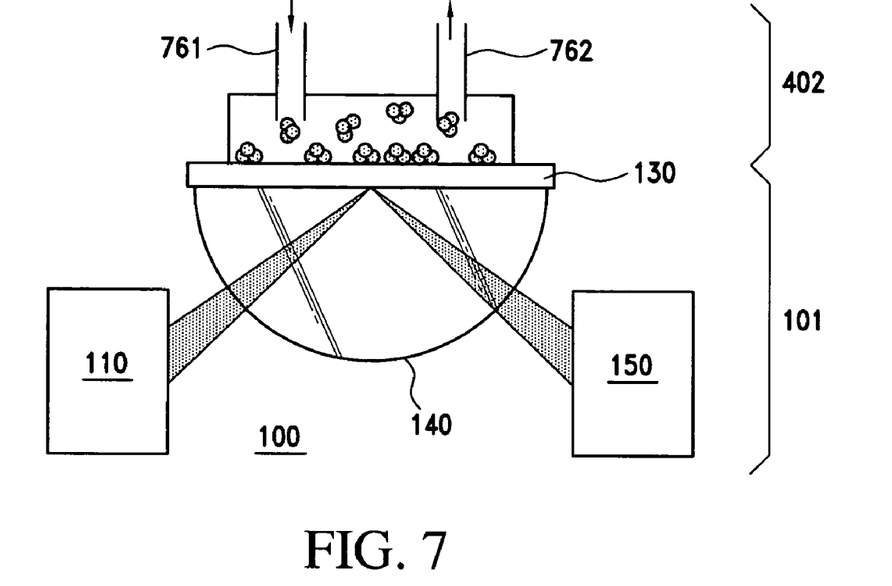
FIG. 7 illustrates a partial cross-sectional, schematic view of the first and second portions of the apparatus in accordance with a different embodiment of the invention.

FIG. 7 illustrates a partial cross-sectional, schematic view of first portion 101 (FIG. 1) and second portion 402 (FIG. 4) of apparatus 100, in accordance with a gas flow cell embodiment. In FIG. 7, portion 402 is illustrated to be a gas flow cell for gas phase measurements, and has an inlet or other input port 761 and an outlet or other output port 762. As an example, the gas flow cell can be used to detect chemical vapors by coating material 130 with a sensing material, such as a polymer, so that apparatus 100 can detect adsorption of gas phase molecules as a change in the SPR angle. In this embodiment, apparatus 100 can be used in many chemical vapor sensor applications including fundamental solid-gas interface studies, detection of toxic molecules in the environment, and chemical analysis of human breath for medical research.

Figure 8:
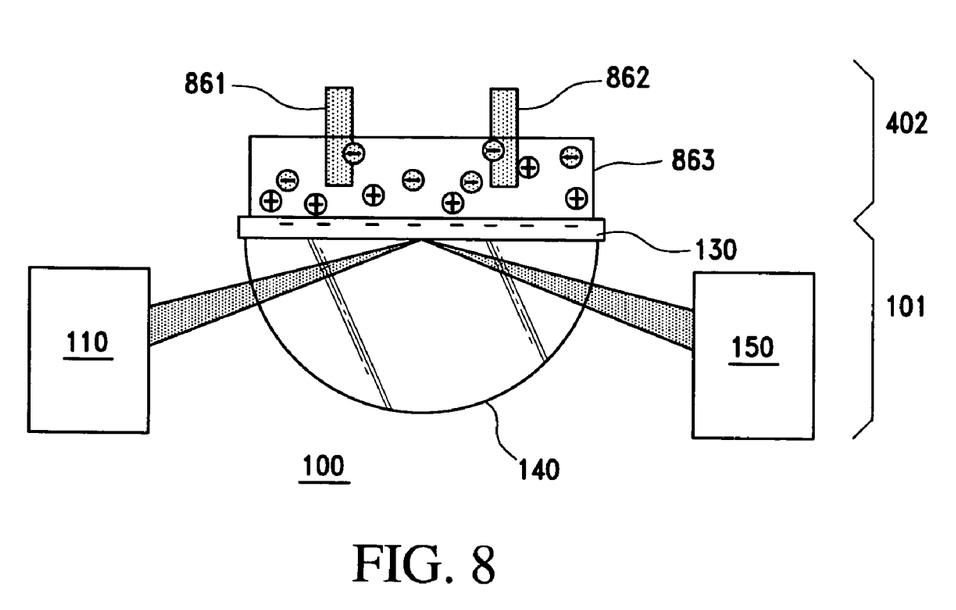
FIG. 8 illustrates a partial cross-sectional, schematic view of the first and second portions of the apparatus in accordance with another embodiment of the invention.

FIG. 8 illustrates a partial cross-sectional, schematic view of first portion 101 (FIG. 1) and second portion 402 (FIG. 4) of apparatus 100, in accordance with an electrochemical cell embodiment. In FIG. 8, portion 402 is illustrated to be an electrochemical cell for electrochemical measurements, and has a reference electrode 861 and a counter electrode 862 in a chamber 863. The electrochemical cell can also implement coupled voltammetric techniques, which, when combined with the SPR technique, can provide information regarding various electrochemical phenomena and processes occurring at the solid-liquid interface such as, for example, charge-induced molecular adsorption and desorption, structural changes of adsorbates, electrodeposition, and anodic stripping. In this embodiment, apparatus 100 can be used in many electrochemical SPR applications including anodic stripping analysis, electropolymerization, electrodeposition, corrosion, conformal changes of immobilized redox molecules, charge transfer processes, and potential-controlled molecular adsorption processes.

Figure 9:
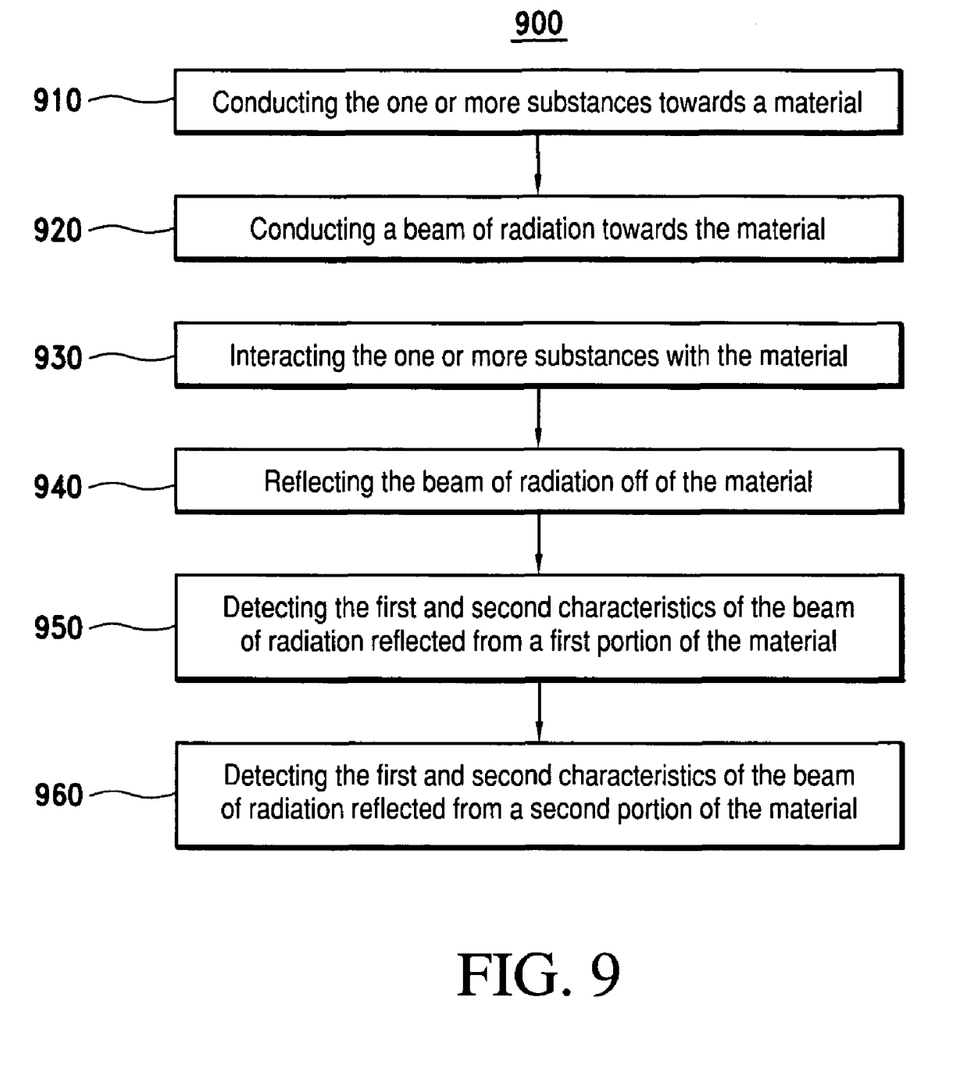
FIG. 9 illustrates a flow chart of a method for detecting a substance in accordance with an embodiment of the invention.

FIG. 9 illustrates a flow chart 900 of a method for detecting one or more substances. Flow chart 900 includes a step 910 for conducting the one or more substances towards a material. As an example, channels 421 and 431 (FIG. 4), channel 521 and 531 (FIG. 5), input port 661, input port 761, and/or chamber 863 can perform step 910 by conducting the one or more substances towards a first surface of material 130 (FIG. 1).

Flow chart 900 also includes a step 920 for conducting a beam of radiation towards the material. As an example, system 110 and/or system 210 can perform step 920 by conducting the beam of radiation towards a second surface of material 130 (FIG. 1), which is opposite or otherwise different from the first surface of material 130. Also, the beam of radiation in step 920 can be similar to radiation 120 (FIG. 1) and/or radiation 220 (FIG. 2).

Flow chart 900 further includes a step 930 for interacting the one or more substances with the material. As an example, step 930 can include interacting the one or more substances with the first surface of material 130.

Flow chart 900 additionally includes a step 940 for reflecting the beam of radiation off of the material. As an example, step 940 can include reflecting the beam of radiation off of the second surface of material 130. The beam of radiation can have a first characteristic before the material interacts with one or more substances and can have a second characteristic while and/or after the material interacts with the one or more substances. The sequence of steps 910, 920, 930, and 940 are interchangeable and can be repeated. Steps 910, 920, 930, and 940 can also be performed simultaneously with each other.

Flow chart 900 continues with a step 950 for detecting the first and second characteristics of the beam of radiation reflected from a first portion of the material. As an example, system 150 and/or system 350 can be used to perform step 950.

Flow chart 900 also includes a step 960 for detecting the first and second characteristics of the beam of radiation reflected from a second portion of the material. As an example, system 150 and/or system 350 can be used to perform step 960. The sequence of steps 950 and 960 are interchangeable and can be repeated. Steps 950 and 960 can also be performed simultaneously with each other, as well as with steps 910, 920, 930, and 940.

Although the invention has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. It is intended that the scope of the invention shall be limited only to the extent required by the appended claims. For example, to one of ordinary skill in the art, it will be readily apparent that the methods discussed herein may be implemented in a variety of embodiments, and that the foregoing discussion of certain of these embodiments does not necessarily represent a complete description of all possible embodiments. Accordingly, the detailed description of the drawings, and the drawings themselves, disclose at least one preferred embodiment of the invention, and may disclose alternative embodiments of the invention.

All elements claimed in any particular claim are essential to the invention claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A surface plasmon resonance apparatus for detecting a substance comprising:
   a metallic layer comprising first and second metallic regions;
   a dielectric body adjacent to the metallic layer;
   a light projection system to project a light beam through the dielectric body and onto the metallic layer to create a surface plasmon resonance at an interface between the metallic layer and the substance;
   a beam reflector;
   a beam splitter; and
   a light detection system comprising at least two light beam sensors to detect a reflection of the light beam from the metallic layer;
   wherein:
     the reflection of the light beam comprises:

a first light beam portion reflected off the first metallic region; and
a second light beam portion reflected off the second metallic region;
a first light beam sensor of the at least two light beam sensors comprises a first position sensitive photodetector;
a second light beam sensor of the at least two light beam sensors comprises a second position sensitive photodetector;
the beam reflector is configured to reflect the reflection of the light beam from the metallic layer towards the beam splitter;
the beam splitter is configured to:
direct the first light beam portion from the beam reflector towards the first light beam sensor; and
direct the second light beam portion from the beam reflector towards the second light beam sensor;
the first light beam sensor is configured to:
receive the first light beam portion of the reflection of the light beam at the first position sensitive photodetector; and
continuously detect a change in an intensity distribution of the first light beam portion along a length of the first position sensitive photodetector to generate a first surface plasmon resonance signal; and
the second light beam sensor is configured to:
receive the second light beam portion of the reflection of the light beam at the second position sensitive photodetector; and
continuously detect a change in an intensity distribution of the second light beam portion along a length of the second position sensitive photodetector to generate a second surface plasmon resonance signal.

2. The surface plasmon resonance apparatus of claim 1 wherein:
each of the at least two light beam sensors has positions adjustable relative to the metallic layer and the dielectric body.

3. The surface plasmon resonance apparatus of claim 1 wherein:
the first light beam sensor is devoid of detecting the second light beam portion reflected from the second metallic region; and
the second light beam sensor is devoid of detecting the first light beam portion reflected from the first metallic region.

4. The surface plasmon resonance apparatus of claim 1 wherein:
the first and second metallic regions are capable of being electrically or electrochemically biased.

5. The surface plasmon resonance apparatus of claim 1 wherein:
at least one of the first or second surface plasmon resonance signals is used as a reference signal.

6. The surface plasmon resonance apparatus of claim 1 wherein:
the light projection system further comprises:
a cylindrical lens to focus the light beam onto the metallic layer.

7. The surface plasmon resonance apparatus of claim 1 wherein:
the light projection system projects the light beam as a single beam onto the metallic layer.

8. The surface plasmon resonance apparatus of claim 1 wherein:
the light projection system further comprises:
a light beam splitter to split the light beam into at least the first and second portions.

9. The surface plasmon resonance apparatus of claim 8 wherein:
the light projection system further comprises:
a cylindrical lens to focus the first and second portions of the light beam onto the metallic layer.

10. The surface plasmon resonance apparatus of claim 1 wherein:
the first metallic region has a first composition; and
the second metallic region has a second composition different from the first composition.

11. The surface plasmon resonance apparatus of claim 1 wherein:
the first metallic region has a first composition; and
the second metallic region has the first composition.

12. The surface plasmon resonance apparatus of claim 1 wherein:
the first and second light beam portions are conducted through the same optical guides before being detected by the at least two light beam sensors.

13. The surface plasmon resonance apparatus of claim 1 wherein:
the first and second metallic regions of the metallic layer are electrically isolated from each other and are capable of being electrically or electrochemically biased independently of each other.

14. The surface plasmon resonance apparatus of claim 1 wherein:
the light detection system further comprises an imaging device; and
the beam reflector is partially transparent and directs a portion of the light beam to the imaging device.

15. The surface plasmon resonance apparatus of claim 1 wherein:
the light projection system is configured to project a second light beam through the dielectric body and onto the metallic layer at a different angle than the light beam;
when the substance comprises a liquid:
the first and second position sensitive photodetectors detect the reflection of the light beam; and
when the substance comprises a gas:
the first and second position sensitive photodetectors detect a reflection of the second light beam.

16. The surface plasmon resonance apparatus of claim 15 wherein:
the light projection system further comprises:
a first light beam source to project the light beam when the substance comprises the liquid; and
a second light beam source to project the second light beam when the substance comprises the gas.

17. The surface plasmon resonance apparatus of claim 1 further comprising:
an assembly to conduct the substance towards the interface of the metallic layer,
wherein:
the assembly aligns the substance to the light beam.

18. The surface plasmon resonance apparatus of claim 17 wherein:
the assembly further comprises:
a cell having one or more flow channels through which the substance is conducted towards and away from the metallic layer; and a gasket having one or more flow channels through which the substance is conducted from the cell towards the metallic layer and from the metallic layer towards the cell.

19. The surface plasmon resonance apparatus of claim 18 wherein:
the gasket has one or more openings to expose the metallic layer to the substance; and
the assembly aligns the one or more openings in the gasket to the first and second regions of the metallic layer reflecting the light beam.

20. The surface plasmon resonance apparatus of claim 19 wherein:
the assembly further comprises:
a self-alignment mechanism to align the one or more openings in the gasket the first and second regions of the metallic layer reflecting the light beam.

21. The surface plasmon resonance apparatus of claim 18 wherein:
the one or more flow channels in the cell comprise two or more flow channels;
the one or more flow channels in the gasket comprise two or more flow channels;
a first one of the two or more flow channels in the cell is coupled to a first one of the two or more flow channels in the gasket;
a second one of the two or more flow channels in the cell is coupled to a second one of the two or more flow channels in the gasket;
the substance is conducted through the first one of the two or more flow channels in the cell and the first one of the two or more flow channels in the gasket; and
a second substance, different from the substance, is conducted through the second one of the two or more flow channels in the cell and the second one of the two or more flow channels in the gasket.

22. The surface plasmon resonance apparatus of claim 18 wherein:
the assembly further comprises:
a holder to support and seal the cell and the gasket over the metallic layer, the holder comprising:
one or more input ports to introduce the substance into the assembly; and
one or more output ports to remove the substance from the assembly;
the cell and the gasket are capable of being removed from the holder;
the holder is capable of supporting and sealing other cells and gaskets over the metallic layer; and
the cell and the other cells are selected from the group consisting of liquid flow cells, electrochemical cells, and gas flow cells.

23. The surface plasmon resonance apparatus of claim 17 wherein:
the assembly further comprises:
one or more input ports to introduce the substance into the assembly.

24. The surface plasmon resonance apparatus of claim 17 wherein:
the assembly further comprises:
one or more output ports to remove the substance from the assembly.

25. The surface plasmon resonance apparatus of claim 1 wherein:
the at least two light beam sensors are adjustably positionable relative to each other.

26. The surface plasmon resonance apparatus of claim 1 wherein:
the first light beam sensor is configured for continuous detection of the change in the intensity distribution of the first light beam portion throughout substantially the entire length of the first position sensitive photodetector; and
the second light beam sensor is configured for continuous detection of the change in the intensity distribution of the second light beam portion throughout substantially the entire length of the second position sensitive photodetector.

27. The surface plasmon resonance apparatus of claim 1 wherein:
the first position sensitive photodetector comprises a first resistance that is sensitive to the first light beam portion along the length of the first position sensitive photodetector;
the first light beam sensor is configured to detect a first resistance change of the first resistance at a first zone of the length of the first position sensitive photodetector when the intensity distribution of the first light beam portion changes with respect to the first zone; and
the first resistance change is local to the first zone.

28. The surface plasmon resonance apparatus of claim 27 wherein:
the second position sensitive photodetector comprises a second resistance that is sensitive to the second light beam portion along the length of the second position sensitive photodetector;
the second light beam sensor is configured to detect a second resistance change of the second resistance at a second zone of the length of the second position sensitive photodetector when the intensity distribution of the second light beam portion changes with respect to the second zone;
the second resistance change is local to the second zone;
the first position sensitive photodetector comprises a first monolithic PIN photodiode; and
the second position sensitive photodetector comprises a second monolithic PIN photodiode.

29. A surface plasmon resonance apparatus for detecting a substance, comprising:
a metallic layer;
a dielectric body adjacent to the metallic layer;
a light projection system to project a light beam through the dielectric body and onto the metallic layer to create a surface plasmon resonance at an interface between the metallic layer and the substance; and
a light detection system comprising at least two light beam sensors to detect a reflection of the light beam from the metallic layer and to generate a surface plasmon resonance signal for each of the at least two light beam sensors,
wherein:
each of the at least two light beam sensors comprises a position sensitive photodetector;
the light projection system further comprises a light beam splitter to split the light beam into at least first and second portions;
a first portion of the metallic layer reflects the first portion of the light beam;
a second portion of the metallic layer reflects the second portion of the light beam;
a first one of the at least two light beam sensors detects the first portion of the light beam reflected from the second portion of the metallic layer;

a second one of the at least two light beam sensors detects the second portion of the light beam reflected from the second portion of the metallic layer;

the first one of the at least two light beam sensors is devoid of detecting the second portion of the light beam reflected from the second portion of the metallic layer; and the second one of the at least two light beam sensors is devoid of detecting the first portion of the light beam reflected from the first portion of the metallic layer; and the light beam splitter comprises:
a lateral displacement prism; and
a beam defocusing mechanism.

30. The surface plasmon resonance apparatus of claim 29 wherein:
at least one of the surface plasmon resonance signals is used as a reference signal.

31. The surface plasmon resonance apparatus of claim 29 wherein:
the light detection system further comprises:
a beam reflector.

32. The surface plasmon resonance apparatus of claim 29 wherein:
the light projection system configured to convergently focus the light beam towards the metallic layer.

33. A surface plasmon resonance apparatus for detecting a substance, comprising:
a metallic layer;
a dielectric body adjacent to the metallic layer;
a light projection system to project a light beam through the dielectric body and onto the metallic layer to create a surface plasmon resonance at an interface between the metallic layer and the substance; and
a light detection system comprising at least two light beam sensors to detect a reflection of the light beam from the metallic layer and to generate a surface plasmon resonance signal for each of the at least two light beam sensors,
wherein:
each of the at least two light beam sensors comprises a position sensitive photodetector;
the light detection system further comprises a beam reflector;
the light detection system further comprises a beam splitter;
the beam reflector reflects the light beam from the metallic layer towards the beam splitter;
the beam splitter directs the light beam from the beam reflector towards the at least two light beam sensors; and
the at least two light beam sensors are located on opposite sides of the beam splitter.

34. The surface plasmon resonance apparatus of claim 33 wherein:
the beam splitter is a right-angle reflector.

35. The surface plasmon resonance apparatus of claim 33, wherein:
the light projection system is configured to project a second light beam through the dielectric body and onto the metallic layer at a different angle than the light beam;
when the substance comprises a liquid:
the first and second position sensitive photodetectors detect the reflection of the light beam; and
when the substance comprises a gas:
the first and second position sensitive photodetectors detect a reflection of the second light beam.

36. A method of detecting one or more substances comprising:
conducting the one or more substances towards a material;
conducting a beam of radiation towards the material;
interacting the one or more substances with the material;
reflecting the beam of radiation off of the material, the beam of radiation having, after reflected off of the material, a first characteristic before the material interacts with one or more substances, and a second characteristic while the material interacts with the one or more substances;
detecting the first and second characteristics of the beam of radiation reflected from a first portion of the material; and
detecting at least one of the first or second characteristics of the beam of radiation reflected from a second portion of the material;
wherein:
the material comprises a dielectric layer and a metallic layer;
the first portion of the material comprises a first metallic region of the metallic layer;
the second portion of the material comprises a second metallic region of the metallic layer;
conducting the beam of radiation towards the material comprises:
projecting the beam of radiation to pass through the dielectric layer and onto the metallic layer;
interacting the one or more substances with the material comprises:
generating a surface plasmon resonance at an interface between the metallic layer and the one or more substances;
reflecting the beam of radiation off of the material comprises:
reflecting a first beam portion of the beam of radiation off the first metallic region; and
reflecting a second beam portion of the beam of radiation off the second metallic region;
detecting the first and second characteristics of the beam of radiation reflected from the first portion of the material comprises:
receiving, with a first position sensitive photodetector, the first beam portion without the second beam portion; and
continuously detecting along a length of the first position sensitive photodetector for a change in an intensity distribution of the first beam portion;
detecting the at least one of the first or second characteristics of the beam of radiation reflected from the second portion of the material comprises:
receiving, with a second position sensitive photodetector, the second beam portion without the first beam portion; and
continuously detecting along a length of the second position sensitive photodetector for a change in an intensity distribution of the second beam portion; and
reflecting the beam of radiation off of the material further comprises:
reflecting the beam of radiation towards a beam splitter;
reflecting the first beam portion off of the beam splitter towards the first position sensitive photodetector; and reflecting the second beam portion off of the beam splitter towards the second position sensitive photodetector.

37. The method of claim 36 wherein:
conducting the one or more substances further comprises:
conducting the one or more substances towards a first surface of the metallic layer;
conducting the beam of radiation further comprises:
conducting the beam of radiation towards a second surface of the metallic layer, the second surface different from the first surface;
interacting the one or more substances further comprises:
interacting the one or more substances with the first surface of the metallic layer; and
reflecting the beam of radiation further comprises:
reflecting the beam of radiation off of the second surface of the metallic layer.

38. The method of claim 36 wherein:
reflecting the beam of radiation towards the beam splitter comprises:
reflecting the beam of radiation off of the material towards a beam reflector; and
reflecting the beam of radiation off of the beam reflector towards the beam splitter.

39. The method of claim 38 further comprising:
locating the first and second position sensitive photodetectors on opposite sides of the beam splitter.

40. The method of claim 36 wherein:
continuously detecting for the change in the intensity distribution of the first beam portion comprises:
continuously detecting for the change in the intensity distribution of the first beam portion throughout substantially the entire length of the first position sensitive photodetector; and
continuously detecting for the change in the intensity distribution of the second beam portion comprises:
continuously detecting for the change in the intensity distribution of the second beam portion throughout substantially the entire length of the second position sensitive photodetector.

41. The method of claim 36 wherein:
the first position sensitive photodetector comprises a first resistance that is sensitive to the first beam portion along the length of the first position sensitive photodetector;
continuously detecting for the change in the intensity distribution of the first beam portion comprises:
detecting a first resistance change of the first resistance at a first zone of the length of the first position sensitive photodetector when the intensity distribution of the first beam portion changes with respect to the first zone;
and
the first resistance change is local to the first zone.

42. The method of claim 41 wherein:
the second position sensitive photodetector comprises a second resistance that is sensitive to the second beam portion along the length of the second position sensitive photodetector;
continuously detecting for the change in the intensity distribution of the second beam portion comprises:
detecting a second resistance change of the second resistance at a second zone of the length of the second position sensitive photodetector when the intensity distribution of the second beam portion changes with respect to the second zone;
the second resistance change is local to the second zone;
the first position sensitive photodetector comprises a first monolithic PIN photodiode; and
the second position sensitive photodetector comprises a second monolithic PIN photodiode.

43. The method of claim 36 wherein:
conducting the beam of radiation towards the material comprises:
convergently focusing the beam of radiation towards the metallic layer.

44. A method of detecting one or more substances comprising:
conducting the one or more substances towards a material;
conducting a beam of radiation towards the material;
interacting the one or more substances with the material;
reflecting the beam of radiation off of the material, the beam of radiation having, after reflected off of the material, a first characteristic before the material interacts with one or more substances, and a second characteristic while the material interacts with the one or more substances;
detecting the first and second characteristics of the beam of radiation reflected from a first portion of the material; and
detecting at least one of the first or second characteristics of the beam of radiation reflected from a second portion of the material;
wherein:
the material comprises a dielectric layer and a metallic layer;
the first portion of the material comprises a first metallic region of the metallic layer;
the second portion of the material comprises a second metallic region of the metallic layer;
conducting the beam of radiation towards the material comprises:
projecting the beam of radiation to pass through the dielectric layer and onto the metallic layer;
interacting the one or more substances with the material comprises:
generating a surface plasmon resonance at an interface between the metallic layer and the one or more substances;
reflecting the beam of radiation off of the material comprises:
reflecting a first beam portion of the beam of radiation off the first portion of the material; and
reflecting a second beam portion of the beam of radiation off the second portion of the material;
detecting the first and second characteristics of the beam of radiation reflected from the first portion of the material comprises:
receiving, with a first position sensitive photodetector, the first beam portion without the second beam portion; and
continuously detecting along a length of the first position sensitive photodetector for a change in an intensity distribution of the first beam portion;
detecting the at least one of the first or second characteristics of the beam of radiation reflected from the second portion of the material comprises:
receiving, with a second position sensitive photodetector, the second beam portion without the first beam portion; and
continuously detecting along a length of the second position sensitive photodetector for a change in an intensity distribution of the second beam portion;

conducting the beam of radiation towards the material comprises:
  conducting a first beam of radiation towards the material at a first angle when the one or more substances are liquid; and
  conducting a second beam of radiation towards the material at a second angle different than the first angle when the one or more substances are gaseous;
and receiving, with the first position sensitive photodetector, the first beam portion without the second beam portion comprises:
  receiving at the first position sensitive photodetector at least a portion of the first beam of radiation when the one or more substances are liquid; and
  receiving at the first position sensitive photodetector at least a portion of the second beam of radiation when the one or more substances are gaseous.

* * * * *